United States Patent
Czernuszka et al.

(10) Patent No.: US 6,589,590 B2
(45) Date of Patent: Jul. 8, 2003

(54) COMPOSITE MATERIAL AND METHODS OF MAKING THE SAME

(75) Inventors: Jan Tadeusz Czernuszka, Oxford (GB); Alison Christina Lawson, Northwich (GB); Alasdair Hamish Robert Wallace Simpson, Oxford (GB)

(73) Assignee: Isis Innovation Limited, Oxford (GB)

( * ) Notice: Subject to any disclaimer, the term of this patent is extended or adjusted under 35 U.S.C. 154(b) by 0 days.

(21) Appl. No.: 10/083,570

(22) Filed: Feb. 27, 2002

(65) Prior Publication Data

US 2002/0133238 A1 Sep. 19, 2002

Related U.S. Application Data

(62) Division of application No. 09/287,174, filed on Apr. 6, 1999, now Pat. No. 6,395,036.
(60) Provisional application No. 60/080,776, filed on Apr. 6, 1998.

(51) Int. Cl.⁷ .......................... A61L 27/00; B05D 1/18; B05D 1/34
(52) U.S. Cl. ...................... 427/2.1; 427/2.24; 427/2.26; 427/2.27; 427/2.3; 427/2.31; 427/209; 427/402; 427/430.1; 514/21; 514/12; 530/352; 530/356; 530/840; 424/484
(58) Field of Search ............................... 427/2.1, 2.24, 427/2.26, 2.27, 2.3, 2.31, 209, 402, 430.1; 514/21, 12; 530/352, 356, 840; 424/484

(56) References Cited

U.S. PATENT DOCUMENTS

| | | | |
|---|---|---|---|
| 4,957,509 A | 9/1990 | Tamari et al. | 623/16 |
| 5,591,234 A | 9/1990 | Kirsch | 623/16 |
| 5,306,311 A * | 4/1994 | Stone et al. | 623/14.12 |
| 5,508,267 A * | 4/1996 | Czernuszka et al. | 514/21 |
| 5,532,217 A * | 7/1996 | Silver et al. | 514/21 |
| 6,201,039 B1 | 3/2001 | Brown et al. | 523/115 |
| 6,214,049 B1 | 4/2001 | Gayer et al. | 623/16.11 |
| 6,228,117 B1 | 5/2001 | De Bruijn et al. | 623/16.11 |
| 6,231,615 B1 | 5/2001 | Preissman | 623/23.73 |

OTHER PUBLICATIONS

M. Iijima et al., "Oriented growth of octacalcium phosphate crystals on type I collagen fibrils under physiological conditions", Journal of Crystal Growth, vol. 140, 1994, pp. 91–99.

* cited by examiner

Primary Examiner—Shrive P. Beck
Assistant Examiner—Jennifer Kolb Michener
(74) Attorney, Agent, or Firm—Wenderoth, Lind & Ponack, L.L.P.

(57) ABSTRACT

A method of making artificial bone comprises providing a membrane of collagen with solutions of calcium ions and of phosphate ions on opposite sides of the membrane. The calcium ions and phosphate ions diffuse through the membrane and precipitate as a hydroxyapatite material. Control of ionic concentrations ensures that precipitation takes place within the fibrils of the membrane. The result is an artificial bone material comprising a matrix of collagen and a hydroxyapatite material deposited within the matrix.

15 Claims, 3 Drawing Sheets

COMPOSITE MATERIAL AND METHODS OF MAKING THE SAME

This application is a Divisional application of Ser. No. 09/287,174, filed Apr. 6, 1999, now U.S. Pat. No. 6,395,036, which claims the benefit of U.S. provisional application Ser. No. 60/080,776, filed Apr. 6, 1998.

BACKGROUND OF THE INVENTION

Collagen is widely accepted as having suitable biological properties for use as a biomaterial and has been used in a variety of surgical applications. Such applications include bioprosthetic heart valves, tendon prostheses, vascular grafts and wound repair. In some cases, the collagen is biodegradable and is ultimately completely replaced by natural tissue, in others the collagen has been treated to render it essentially non-degradable.

The use of calcium phosphate ceramics in hard tissue repair and replacement has been investigated extensively for a number of years. These ceramics are available in a number of compositions; hydroxyapatite, modified hydroxyapatite and a hydroxyapatite-tricalcium phosphate composite. Both porous and fully dense ceramics are in use. These materials show excellent biocompatibility, exhibiting good bone bonding and osteoconductivity, but are unsuitable for use in load bearing sites as the mechanical properties, especially the fatigue strength, are inadequate.

Bone is a composite of calcium phosphate with collagen, and the interaction of the hard brittle ceramic phase and the pliant organic matrix give bone its unique mechanical properties. Thus a logical step in the development of the ideal bone substitute is to mimic the structure of bone and mix collagen and calcium phosphate. Such composites have been produced by mixing calcium phosphate granules with a collagen web or mixing calcium phosphate particles with a collagen suspension. More recently, methods have focused on the precipitation of calcium phosphate onto a preformed collagen matrix.

A diffusion based method has been used to precipitate octacalcium phosphate onto rat tail collagen discs. Another author precipitated hydroxyapatite onto collagen by enclosing collagen fibrils in a semipermeable cellulose membrane and allowing ions to diffuse through the cellulose-collagen assembly. In this case the cellulose membrane was controlling the diffusion of the ions and the collagen was suspended in a calcium phosphate solution.

BRIEF SUMMARY OF THE INVENTION

However, materials prepared in this way are limited in the extent to which they can match the properties of bone, because mineral nucleation in the natural material occurs not only on the surface of the fibres, but within the collagen fibrils. To force the precipitation of calcium phosphate inside collagen fibrils the inventors have developed a diffusion based method, in which the calcium and phosphate ions migrate into the collagen matrix from opposite sides and precipitate where they meet: inside the collagen membrane. They have precipitated hydroxyapatite on and within a collagen sheet, using the collagen membrane to separate reservoirs of calcium and phosphate ions. The relative concentrations of the two ions have been adjusted to ensure precipitation occurs inside the membrane.

In one aspect the invention provides a method of making a composite material suitable for use as artificial bone, which method comprises providing a membrane of a biocompatible hydrophilic organic polymer, a solution of calcium ions adjacent a first surface of the membrane, a solution of phosphate ions adjacent a second surface of the membrane, and causing calcium ions and phosphate ions diffusing through the membrane to meet and precipitate as a hydroxyapatite material.

In another aspect the invention provides a composite material suitable for use as artificial bone, comprising a matrix of a biocompatible hydrophilic organic polymer and a hydroxyapatite material deposited within the matrix.

In another aspect the invention provides a composite material suitable for use as artificial bone, comprising a membrane of a biocompatible hydrophilic organic polymer and a hydroxyapatite material deposited within the membrane, or a product formed by pressing into a desired shape the said membrane.

DETAILED DESCRIPTION OF THE INVENTION

Figure 1:
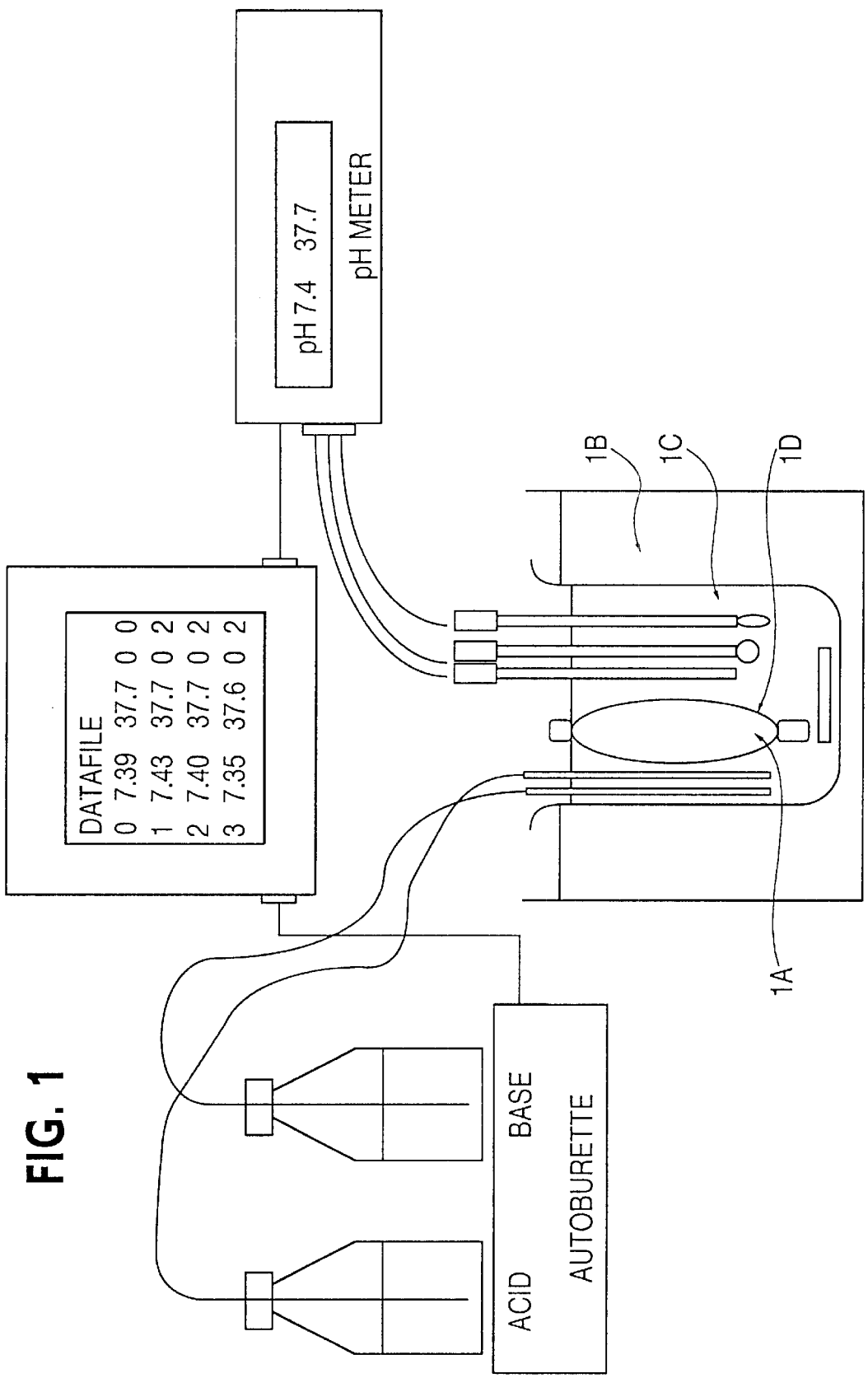
FIG. 1 is a schematic diagram of the apparatus used for the experiments described in the example. Reference numbers 1A, 1B, 1C and 1D, shown in the Figure, represent Calcium solution ("1A"), Water bath 37° C. ("1B"), Phosphate solution ("1C") and Collagen ("1D"), respectively.

The biocompatible hydrophilic organic polymer may be one of a variety of materials known or tested for use in artificial bone, including cellulose, chitin, polylactic acid, polyglycollic acid, polyhydroxybutyric acid and salts and esters thereof. Preferably the polymer is collagen.

The mechanical and biological properties of collagen can be altered by chemical cross-linking. A heavily cross-linked collagen will be more resistant to enzymatic degradation and will also tend to be stiffer than lightly cross-linked material. Thus it is possible to alter the mechanical and biological properties of these composites by cross-linking the collagen sheets prior to calcification. Composites can be produced from collagen cross-linked using a number of chemical treatments including glutaraldehyde and carbodiimide treatments.

The organic molecule O-Phospho-serine (SerP) has been shown to have a profound effect on the nucleation and growth of calcium phosphate in vitro. A chemical treatment to bond SerP or other phosphoprotein to the collagen sheet prior to calcification can also be used.

In the method of the invention, a solution of calcium ions is maintained against one surface of the membrane, and a solution of phosphate ions is maintained against the other surface of the membrane. The properties of the solutions are controlled to achieve various desired effects as described below.

The solution of calcium ions may conveniently be based on calcium chloride or calcium nitrate. The pH of the solution may preferably from 7.0 to 9.0, particularly from 7.5 to 8.5. If the pH is too high, the collagen or other biocompatible membrane may be damaged; if the pH is too low, calcium phosphate may be precipitated in an undesired form. The concentration of the solution of calcium ions is preferably 3 mM to 1 M, particularly 10 to 50 mM. If the concentration is too low, the amount of precipitate may be undesirably small; if the concentration is too high, then the crystal size and shape and composition of the precipitate may be difficult to control.

The solution of phosphate ions may conveniently be based on potassium dihydrogen phosphate or other alkali metal phosphate. The pH of the solution is preferably in the range 7.0 to 9.0, particularly 7.5 to 8.5. If the pH is too high, the collagen or other biocompatible membrane may be damaged; if the pH is too low, calcium phosphate may be precipitated in an undesired form. The phosphate ion concentration of the solution is preferably from 3 mM to 1 M, particularly from 20 to 100 mM. If the concentration is too low, then an undesirably small amount of precipitate may form. If the concentration is too high, then the crystal size and shape and composition of the precipitate may be difficult to control.

During performance of the method, calcium ions and phosphate ions diffuse from opposite sides through the membrane. Where they meet, they combine to form a crystalline deposit. Because calcium ions may diffuse at a different rate than phosphate ions, the use of solutions containing equimolar concentrations of calcium ions and phosphate ions may tend to result in a crystalline deposit at or on one side of the membrane. In order to form the desired precipitate within the membrane, it is preferred that the relative concentrations of the calcium and phosphite ions be controlled, e.g. that the phosphate ion concentration in the solution of phosphate ions be higher or lower than the calcium ion concentration in the solution of calcium ions. For example, the phosphate ion concentration may be up to 5 times the calcium ion concentration.

Calcium phosphate may precipitate out of aqueous solution as: dicalcium phosphate dihydrate (Ca/P 2:1); octacalcium phosphate (Ca/P 1.33:1) and hydroxyapatite (Ca/P 1.67:1). The pH of the solutions has an effect in determining the form of the calcium phosphate precipitated. As shown in the examples below, hydroxyapatite materials are precipitated from solutions of pH 7.5 to 8.5 e.g. about 8.0. The pH of one or both solutions may be monitored or controlled during the course of the reaction. It is convenient, though not necessary, that the pH of both solutions be the same, e.g. 7.2–9.0.

Calcium phosphate is present in the composite products of this invention as a hydroxyapatite material, which term is herein used to include not only the stoichiometric compound (Ca/P 1.67:1) but also calcium-phosphate-based apatites which are non-stoichiometric and may contain cation and/or anion substitution (Ca/P 1.40:1–1.80:1).

Apatite, and the hydroxyapatite materials with which this invention is concerned, has a hexagonal crystal structure whereas octacalcium phosphate (OCP) has a triclinic crystal structure. The following further information may be of interest.

| Crystal Structure | HAp<br>Hexagonal<br>P63/m | OCP<br>Triclinic<br>P1 |
| --- | --- | --- |
| a (nm) | 0.9432 | 1.9715 |
| b (nm) | — | 0.9534 |
| c (nm) | 0.6881 | 0.6839 |
| α | | 90.14 |
| β | | 92.52 |
| χ | | 108.67 |

It is important to control the phase of calcium phosphate as they each have a different biological response. For example, OCP is more soluble than Hap and hence is resorbed much faster in vivo.

The method of the invention involves holding the membrane between the two solutions so as to keep the solutions separate, for a time sufficient to achieve a desired deposit. Suitable reaction times are in the range of one hour to one week, e.g. one day, which has the advantage of being faster than known diffusion based methods for making artificial bone. The temperature of the solutions is not critical and may conveniently be 20° C.–50° C. e.g. 37° C. It is preferred to include an alkali metal chloride to increase the ionic concentration of one or both solutions. This makes the pH of a solution easier to monitor. More importantly, high ionic strength helps to keep precipitation at a more even level. Without added potassium chloride or other salt, the rate of precipitation tends to be initially high but to fall rapidly.

Then the membrane is recovered and dried. If suitable reaction conditions have been used, a hydroxyapatite material is found to have been deposited within the membrane. The deposit may be uniform (on a macroscopic level; but not on a microscopic level, for each hydroxyapatite crystal is discrete). Or the deposit may have a controlled distribution profile. Collagen exists in the form of fibrils; under preferred conditions, a crystalline deposit forms within the fibrils rather than merely on their surface. The membrane may be formed, e.g. by cold isostatic pressing, into any desired shape for use as bone substitute. The result of this shaping operation is a product comprising a matrix of collagen (or other biocompatible hydrophilic organic polymer) and a hydroxyapatite material deposited uniformly within the matrix, e.g. deposited within rather than on fibrils of collagen.

The proportion of hydroxyapatite material in the composite material depends on various factors, including the concentrations of the solutions of calcium ions and phosphate ions, and is preferably in the range of 1 to 80% by weight of the weight of the composite material.

EXAMPLE 1

Method

Calcium phosphate is precipitated onto a collagen membrane in a temperature and pH controlled environment. The apparatus is shown in FIG. 1.

A collagen tube ("1D" of FIG. 1) is sealed at the bottom with a high density polymer clamp, filled with calcium solution ("1A" of FIG. 1) (e.g. 30 mM $CaCl_2$ & 0.1M KCl, pH 8.0) and the top sealed with a low density polymer clip. The tube is then placed in a vat of phosphate solution ("1C" of FIG. 1) (e.g. 50 mM $KH_2PO_4$ & 0.1M KCl, pH 8.0). The pH of the solutions are brought to the required value with additions of potassium hydroxide solution. The high density clamp anchors the tube to the bottom of the reaction vessel while the low density clip ensures the tube stays upright during the reaction. The reaction vessel is placed in a water bath at 37° C. ("1B" of FIG. 1) and the pH of the phosphate solution ("1C" of FIG. 1) measured using glass Ag/AgCl pH and reference electrodes and an ionmeter. The solution is stirred using a PTFE covered magnetic stirring bar. The data displayed on the ionmeter is logged by a personal computer every 30 seconds and stored in a data file. The computer was connected to an autoburette and any change in pH triggers the addition of an acidic or basic reagent from the autoburette, thus correcting the change in pH. Mineralisation takes place over a 24 hour period, after which, the collagen is removed from solution and air-dried. The mineralised collagen sheets may then be fabricated into a bulk composite by cold-isostatic pressing into the desired shape.

Results

Figure 2:
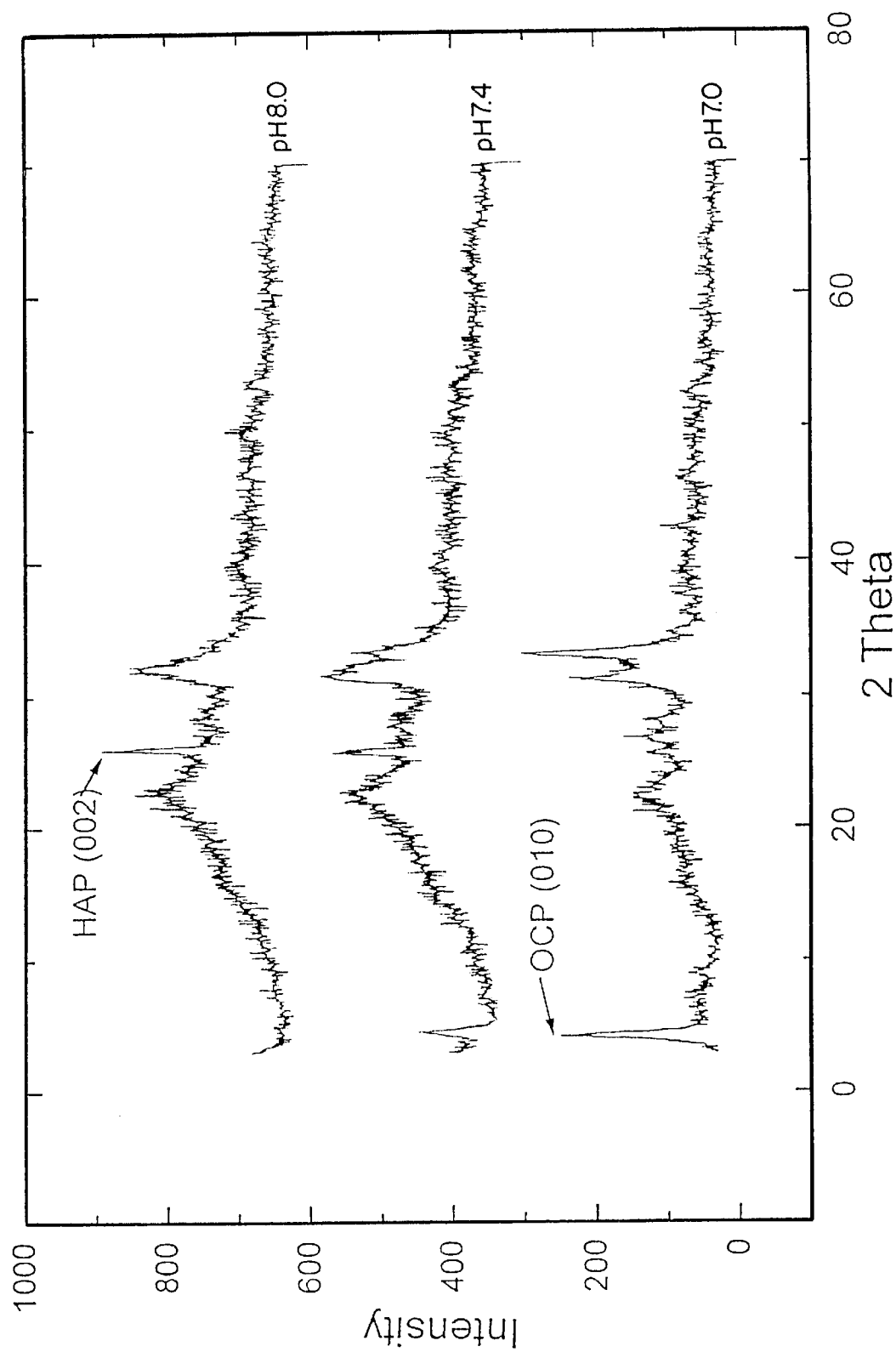
FIG. 2 shows X-ray diffraction patterns of three products, and illustrates the effect of pH on the X-ray diffraction pattern of calcium phosphate precipitated on collagen.

Composites of the octacalcium phosphate and hydroxyapatite form of calcium phosphate have been produced by altering the pH of the solutions. Precipitation at pH 7.0 gives octacalcium phosphate and increasing the pH to 8.0 favours the formation of hydroxyapatite, X-ray diffraction patterns of the precipitate formed at pH 7.0, 7.4 and 8-0 are shown in FIG. 2. A strong (010) octacalcium phosphate peak is visible at pH 7.0. The intensity of this peak is reduced at pH 7.4 and at pH 8.0 it is no longer present, leaving a spectrum characteristic of hydroxyapatite.

With equimolar calcium and phosphate solutions, precipitation occurs as a coating of plate-like crystals on the phosphate side of the membrane. Adjustments of the relative concentrations of the two ions have been made to give a balance between the rates of diffusion of the two ions. Precipitation then occurs inside the collagen membrane. The example concentrations given in the method section, would produce hydroxyapatite precipitation inside the membrane.

The weight percentage mineral can be increased by increasing the concentrations of the two ions. Composites containing in excess of 30 weight percent mineral have been produced.

Figure 3:
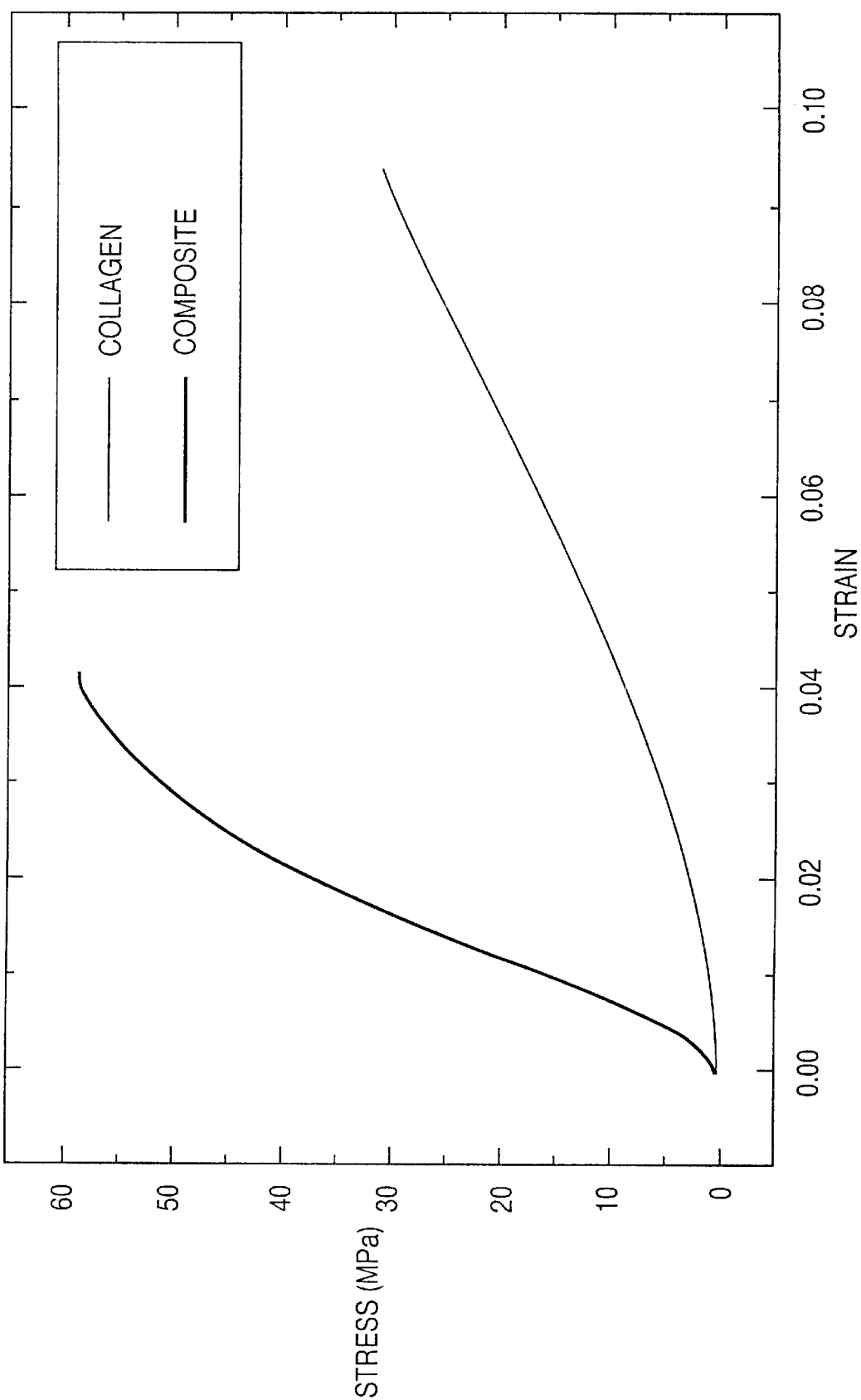
FIG. 3 shows typical stress-strain curves for dry collagen and a composite material according to the invention.

The tensile properties of the collagen sheets have been measured and compared with untreated collagen. Mineralisation increases the stiffness and the ultimate tensile strength of the materials. Typical stress-strain curves for collagen and mineralised collagen are shown in FIG. 3 and examples of the values of ultimate tensile strength (UTS) and Young's Modulus (E) are shown in Table 1. Calcification gives a significant increase in both UTS and Young's Modulus. Comparing composites formed using equimolar concentrations of calcium and phosphate ions i.e. with surface precipitation only, to a composite in which the ionic concentrations were balanced to give precipitation inside the membrane, it has been shown that latter has a significantly higher UTS and Young's Modulus.

TABLE 1

Mechanical properties of collagen-calcium phosphate composites.

| Concentrations [PO$_4$]:[Ca] (mM) | UTS (MPa) | E (MPa) |
|---|---|---|
| 0:0 | 33.65 | 440 |
| 30:30 | 50.65 | 1354 |
| 50:50 | 48.65 | 1246 |
| 50:35 | 54.23 | 1989 |

EXAMPLE 2

Composite materials were produced from collagen cross-linked using a number of chemical treatments include glutaraldehyde and carbodiimide treatments, by the method described in Example 1.

EXAMPLE 3

A chemical treatment to bond O-Phospho-serine to collagen sheet, prior to performing the calcification method described in Example 1, has been investigated.

What is claimed is:

1. A method of making a composite material, which method comprises providing a membrane of a biocompatible hydrophilic organic polymer, a solution of calcium ions but not phosphate ions adjacent to a first surface of the membrane, a solution of phosphate ions but not calcium ions adjacent to a second surface of the membrane, and causing said calcium ions and said phosphate ions diffusing through the membrane to meet and precipitate as a hydroxyapatite material.

2. The method as claimed in claim 1, wherein the biocompatible hydrophilic organic polymer is collagen.

3. The method as claimed in claim 1, wherein said calcium ions and said phosphate ions diffusing through the membrane precipitate as hydroxyapatite.

4. The method as claimed in claim 1, wherein said calcium ions and said phosphate ions diffusing through the membrane are caused to meet and precipitate as hydroxyapatite within the membrane.

5. The method as claimed in claim 1, wherein the solution of calcium ions is based on a calcium salt and has a pH of 7.0 to 9.0.

6. The method as claimed in claim 1, wherein the solution of phosphate ions is based on an alkali metal phosphate and has a pH of 7.0 to 9.0.

7. The method as claimed in claim 1, wherein the solution of calcium ions is at a concentration of 3 mM to 1M and the solution of phosphate ions is at a concentration of 3 mM to 1M.

8. The method as claimed in claim 1, wherein said phosphate ion concentration in said solution of phosphate ions is controlled in relation to said calcium ion concentration in said solution of calcium ions to cause precipitation of the hydroxyapatite material within the membrane.

9. The method as claimed in claim 8, wherein said phosphate ion concentration is up to 5 times said calcium ion concentration.

10. The method as claimed in claim 2, wherein the collagen is cross-linked.

11. The method as claimed in claim 2, wherein the collagen has been pre-treated with O-Phospho-serine.

12. The method as claimed in claim 1, further comprising forming the composite material for use as an artificial bone.

13. The method as claimed in claim 1, further comprising forming the composite material into a desired shape.

14. The method as claimed in claim 1, wherein substantially more of said hydroxyapatite material is formed within the membrane than on the surface of the membrane.

15. The method as claimed in claim 2, wherein substantially more of said hydroxyapatite material is formed within the fibrils of the collagen than on the surface of the collagen.

* * * * *